United States Patent [19]

Takeda

[11] Patent Number: 5,182,950
[45] Date of Patent: Feb. 2, 1993

[54] TENSION TYPE DYNAMIC VISCOELASTICITY MEASURING APPARATUS

[75] Inventor: Haruo Takeda, Tokyo, Japan

[73] Assignee: Seiko Instruments, Inc., Tokyo, Japan

[21] Appl. No.: 783,047

[22] Filed: Oct. 28, 1991

[30] Foreign Application Priority Data

Oct. 29, 1990 [JP] Japan .................................. 2-291052

[51] Int. Cl.$^5$ .......................................... G01N 3/38
[52] U.S. Cl. .................................................. 73/811
[58] Field of Search ................. 73/808, 810, 811, 806, 73/831

[56] References Cited

U.S. PATENT DOCUMENTS 2,936,612  5/1960  Mason .............................. 73/808 X
3,664,179  5/1972  Danko et al. ...................... 73/808 X Primary Examiner—Jerry W. Myracle
Attorney, Agent, or Firm—Spensley Horn Jubas & Lubitz

[57] ABSTRACT

Apparatus for applying an optimal tension exceeding alternating forces to a specimen being measured by automatically detecting saturation of a relaxation phenomenon that has occurred in the specimen when the dynamic viscoelasticity of the specimen is measured by a tension method. The apparatus includes a strain detector for detecting changes in length of the specimen, an electromagnetic force generator for applying a force to the specimen, a moving mechanism for moving the electromagnetic force generator, a movement control unit for controlling the amount of movement of the drive mechanism, a strain differentiation circuit for differentiating the output of the strain detector, and a comparator for comparing the output of the strain differentiation circuit with a target differential value and producing a tension control timing signal. When the drive mechanism is moved or the force produced by the electromagnetic force generator is changed, a relaxation phenomenon occurs in the specimen, with the result that the effective tension and length of the specimen will continue to change for a relaxation time while keeping their proportional relationship. When the output of the strain differentiation circuit becomes less than the target differential value, it can be concluded that the relaxation phenomenon has been saturated so that the comparator can produce the tension control timing signal, making it possible to control the drive mechanism to apply an appropriate tension to the specimen.

2 Claims, 1 Drawing Sheet

TENSION TYPE DYNAMIC VISCOELASTICITY MEASURING APPARATUS

BACKGROUND OF THE INVENTION

The present invention relates to a tension type dynamic viscoelasticity measuring apparatus.

In conventional devices of this kind, a tension control timing signal is output at a predetermined time after the start of the apparatus irrespective of the saturation time of the relaxation phenomenon, such as stress relaxation or creep phenomenon, which has adverse effects on the variations in effective tension of the specimen.

The above-mentioned prior art devices perform the next control at a predetermined time after the start of the apparatus regardless of the saturation of the relaxation phenomenon (creep) that has occurred in the specimen. While this technique has the advantage of being able to perform the tension control quickly when the relaxation phenomenon settles in a shorter time than the preset time, it has a serious disadvantage in that it may on occasion perform the tension control while the specimen is still undergoing the relaxation phenomenon and the effective tension and the resulting length of the specimen are still changing, making the tension control very unstable and, in the worst cases, uncontrollable, which would often result in suspension of the measurement.

Since the effects of the relaxation phenomenon on the measurement vary depending on the temperature and the tension level at which measurement is being taken, it has proven almost impossible to find a preset time which is appropriate under all circumstances.

SUMMARY OF THE INVENTION

Thus, it is an object of the present invention to eliminate such problems experienced with the conventional apparatus and provide a tension type dynamic viscoelasticity measuring apparatus that assures correct and quick measurement for any operator.

The above and other objects, features and advantages of the invention, will be described more fully in the following description, are achieved by the provision of a tension type dynamic viscoelasticity measuring apparatus for measuring viscoelasticity of a specimen which has two opposed ends, which apparatus comprises:

a specimen holder for securely holding one end of the specimen;

a specimen chuck for securely holding the other end of the specimen;

a detection rod having two opposed ends, one of which ends is connected to the specimen chuck;

a strain detector operatively associated with the detection rod for detecting changes in position of the detection rod and producing an output signal representing the position of the detection rod relative to a reference position;

an electromagnetic force generator connected at one end of the detection rod to transmit a force to the specimen via the detection rod and the specimen chuck in response to a force signal;

a drive mechanism connected for moving the electromagnetic force generator in response to a movement signal;

electrical means for generating a force signal and for applying the force signal to the electromagnetic force generator;

movement control means for producing a movement signal and applying the movement signal to the drive mechanism for controlling the amount of movement of the drive mechanism;

signal differentiation means connected for receiving the output signal from the strain detector and producing a differential signal having a value corresponding to the time differential of the output signal from the strain detector;

a target differential value setter for providing a signal having a value corresponding to a selected value of the differential signal; and a comparator connected to receive the differential signal and the signal provided by the target differential value setter when the effective tension in the specimen continues to change for the duration of a relaxation phenomenon that has occurred as a result of the drive mechanism being moved or the electromagnetic force of the electromagnetic force generator being changed in order to control the tension at the specimen to maintain that tension substantially at a control target value;

whereby when the value of the differential signal from the strain differentiation circuit falls below the selected value, the comparator outputs a tension control timing signal indicating that the relaxation phenomenon has ceased.

Preferably, the electrical means include: a dc generator for generating a tension force signal for causing the electromagnetic force generator to impose a tension in the specimen; and a sinusoidal wave generator for generating a sinusoidal wave force signal for causing the electromagnetic force generator to produce a sinusoidal force component.

When the specimen under a certain tension changes in length due to thermal expansion, the change in length is detected by the strain detector. At this time, the effective tension also changes. Hence, the drive mechanism is moved a distance $\Delta L$ by the movement control unit or the dc force of the electromagnetic generator is changed by an amount $\Delta F$ according to the output of the strain detector, or both controls are performed. As a result, a relaxation phenomenon such as stress relaxation or creep occurs in the specimen, so that the strain value output from the strain detector changes greatly at first followed by gradual reduction in the strain variation until the strain converges to a certain value. The effective tension applied to the specimen that is in a proportional relationship with the strain also changes similarly and converges to a certain value. That is, if the amount of change in the strain that has occurred during a certain period of time is known, it is possible to grasp the condition of how the relaxation phenomenon is developing in the specimen. The strain differentiation circuit differentiates the constantly changing strain value signal received from the strain detector and sends the differential values, which provide information on the relaxation saturation, to the comparator. The target differential value setter is preset with a target differential value that represents a rough decision that the relaxation phenomenon has been saturated. The comparator compares the differential value from the strain differentiation circuit with the preset value in the target differential value setter. When the former value falls below the latter, the comparator decides that the relaxation phenomenon that occurred in the specimen has now been saturated and produces at its output a next tension control timing signal permitting an initiation of the tension control by the drive mechanism and/or the dc force of the electromagnetic generator.

Because the measurement is thus not influenced by strain values of the specimen that are constantly changing under the effects of the relaxation phenomenon, it is prevented from becoming an unstable control loop or starting a control loop at unnecessarily long intervals. Hence, a correct and quick dynamic viscoelasticity measurement is assured.

BRIEF DESCRIPTION OF DRAWING

The sole FIGURE is a partly cross-sectional, partly block diagram view of a preferred embodiment of apparatus according to the invention.

DESCRIPTION OF THE PREFERRED EMBODIMENTS

Figure 1:
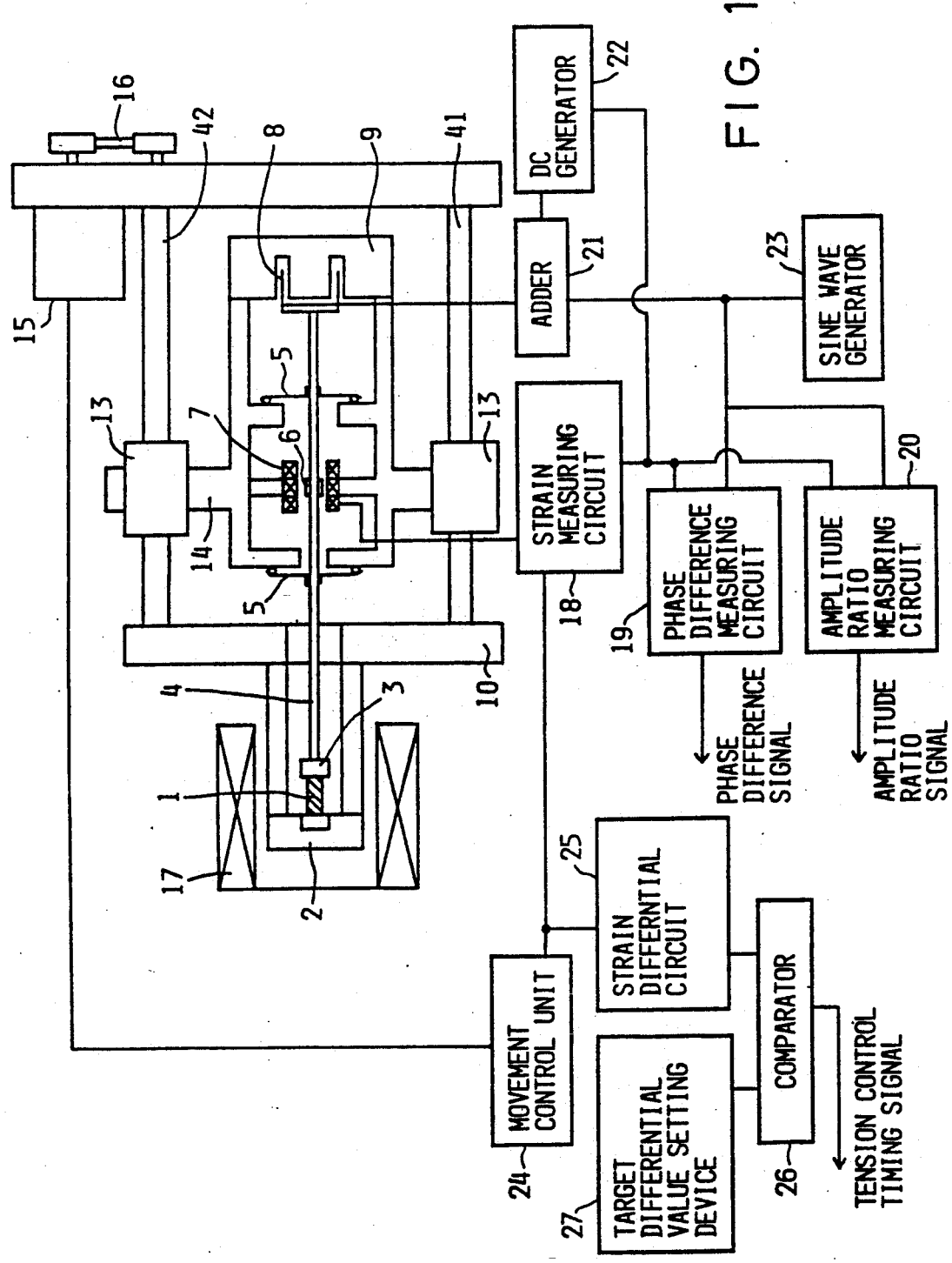

The invention will be described with reference to the sole FIGURE of the drawing which illustrates a preferred embodiment of the invention.

As shown in the FIGURE, a specimen 1 is securely clamped at one end to a specimen holder 2. The other end of specimen 1 is securely held by a specimen chuck 3, which is connected to one end of a detection rod 4. The detection rod 4 is elastically fixed to a mechanism holder 14 via two leaf springs 5 in such a way that the detection rod 4 is allowed to move only in a linear (one-dimensional) direction parallel to the length of specimen 1. The detection rod 4 has a core 6 secured to a portion thereof and core 6 is surrounded by a differential transformer 7 secured in mechanism holder 14 to form a strain detector which detects relative displacement of core 6 as representing strain induced in specimen 1.

Secured at the other end of detection rod 4 is a coil 8 which is surrounded by a magnet 9 secured to mechanism holder 14. The coil 8 and the magnet 9 form an electromagnetic force generator.

A furnace 17 is disposed to surround specimen 1 in order to heat it to a specified temperature.

A sinusoidal wave generator 23 generates a sinusoidal wave whose amplitude is adjusted and sent to an adder 21 where it is added to an output signal from a dc generator 22. The output of adder 21 is applied to the coil 8, which cooperates with magnet 9 to generate a sinusoidal wave force with a superimposed dc component.

The force thus generated produces a strain in specimen 1 via detection rod 4 and specimen chuck 3. The strain induced in specimen 1 is transmitted through the detection rod 4 to the core 6, i.e. core 6 moves through a distance equal to the total strain induced in specimen 1. A signal produced by the differential transformer 7 is fed to a strain measuring circuit 18.

The outputs of sinusoidal wave generator 23 and strain measuring circuit 18 are supplied to a phase difference measuring circuit 19, which produces a phase difference signal. The output of strain measuring circuit 18 is also supplied to dc generator 22. The outputs of the sinusoidal wave generator 23 and the strain measuring circuit 18 are also fed to an amplitude ratio measuring circuit 20, which measures their amplitudes and produces a force-strain amplitude ratio signal. Circuits 19 and 20 are well known in the art.

The mechanism holder 14 is supported via bearings 13 on a ball screw 42 and a guide bar 41. As ball screw 42 is rotated by a drive belt 16, which is driven by a stepping motor 15, mechanism holder 14 is moved to the left or right. The guide bar 41, the ball screw 42, the bearings 13, the stepping motor 15 and the drive belt 16 together form, in a known manner, a drive mechanism for the mechanism holder 14. The stepping motor 15 is operated in accordance with the output of a movement control unit 24.

A strain differential circuit 25 is constructed to differentiates the output signal from strain measuring circuit 18 and sends the resulting differential value signal to a comparator 26. A target differential value signal setter 27 is preset to produce a small differential value signal almost equal to the value which is output from strain differentiation circuit 25 when the relaxation phenomenon in the specimen is saturated. The target differential value signal setter 27 is connected to the comparator 26. The comparator 26 compares the output value from strain differentiation circuit 25 with the preset differential value from target differential value setter 27. When the signal from circuit 25 becomes smaller than the signal from setter 27, the comparator 26 outputs a tension control timing signal.

Now, the operation of the apparatus according to the invention will be described. When, with a dc force generated by the coil 8 and magnet 9 applied, the length of specimen 1 changes due to thermal expansion and softening, the strain experienced by the specimen is measured by strain measuring circuit 18. The movement control unit 24 operates stepping motor 15 so as to drive the drive mechanism in a direction and by an amount to offset the strain to zero, i.e. to bring core 6 to a position relative to transformer 7 such that the signal from transformer 7 indicates a strain of zero.

The canceling of the strain may also be carried out by another control method in which the current value from dc generator 22 is changed to change the dc force generated by electromagnetic force generator 8,9. The control method chosen to reset the strain to zero is determined on the basis of a measuring mode (not shown) selected by an operator.

First, there will be described the control method in which the drive mechanism is moved. As movement control unit 24 drives the stepping motor 15 according to the strain measured by the strain measuring circuit 18, the force produced by motor 15 is transmitted to drive belt 16, ball screw 42, bearing 13, mechanism holder 14, leaf springs 5, detection rod 4, specimen chuck 3 and specimen 1, in that order. The core 6 and the coil 8 secured to detection rod 4 move together with detection rod 4. The other end of specimen 1 is rigidly fixed to specimen holder 2 which, in turn, is secured to a frame base 10. Therefore, the core 6 secured to detection rod 4 moves to a point where the tension in specimen 1 is balanced with the tension produced by electromagnetic force generator 8, 9 minus the recovering force of the springs 5. At this time, specimen 1 is undergoing the relaxation phenomenon such as stress relaxation and creep.

Next, the other control method will be explained in which the dc force produced by electromagnetic force generator 8, 9 is changed. The current value of the output of dc generator 22, which corresponds to the strain measured by the strain measuring circuit 18, is fed to the adder 21 where it is added to the output value (here=0) of sinusoidal wave generator 23. The adder 21 supplies the combined current to the coil 8. The tension, which is produced in proportion to the current supplied to coil 8, is transmitted to the detection rod 4, springs 5, specimen chuck 3, specimen 1, specimen holder 2, and frame base 10. The core 6 secured to detection rod 4 moves to a point where the tension in specimen 1 is balanced by the tension produced by electromagnetic force generator 8, 9 minus the recovering force of the springs 5. At this time, the specimen 1 is undergoing the relaxation phenomenon as when the drive mechanism was controlled.

The relaxation phenomenon in specimen 1 changes the effective tension in specimen 1 for as long as the relaxation phenomenon continues, so that core 6 also continues to change its position during that relaxation time. The position change of the core 6 is detected, on the basis of the output signal from differential transformer 7, by strain measuring circuit 18 which feeds a measured strain value signal to strain differential circuit 25. Strain differential circuit 25 differentiates the strain signal value with respect to time and outputs a differential value to comparator 26. As the relaxation phenomenon in specimen 1 becomes saturated, the positional change of core 6 decreases, converging the output signal from strain differential circuit 25 to zero.

Comparator 26 compares the output signal from strain differential circuit 25 with the preset value from target differential value signal setter 27. When the former is smaller than the latter, comparator 26 outputs a tension control timing signal. The tension control timing signal is a signal indicating that the variation in the effective tension of the specimen due to the relaxation phenomenon has ceased. Hence, if the tension control is resumed when this signal is produced, the tension control based on the strain measured by the strain measuring circuit 18 will become accurate because it is performed only after the relaxation phenomenon is stabilized.

It should be noted that the movement control unit 24, the strain differential circuit 25, the comparator 26 and the target differential value signal setter 27 may be formed either as an analog circuit or as a digital circuit. It is also possible to replace the differential values from strain differential circuit 25 and target differential value signal setter 27 with signal representing changes in the strain over arbitrary time intervals. Further, stepping motor 15 may be replaced with some other kind of motor. These changes or selections can be made without deviating from the spirit of the invention.

This invention provides the strain differential circuit, the comparator, and the target differential value signal setter, these forming a means to automatically detect when the relaxation phenomenon that occurred in the specimen has ceased. This means enables a correct and quick tension control even when the relaxation phenomenon interferes with the control loop, thus contributing to widening the range to which the tension type dynamic viscoelasticity measuring apparatus can be applied.

In view of the description presented above, operation of a system according to the present invention involves the following three basic procedures:

during the first procedure, when strain measuring circuit 18 detects a change in the strength, or resistance to elongation, of specimen 1, strain measuring circuit 18 produces an output signal which is sent to movement control unit 24 and/or dc generator 22 so as to produce an action which has the effect of cancelling the strain value;

in the second procedure, when the output signal from strain measuring circuit 18 indicates a further change in the strength of specimen 1, caused by creep or the like, the strain measuring value output from circuit 18 is differentiated by strain differential circuit 25 and the output of circuit 25 is compared, in comparator 26, with the target differential value produced by device 27. When the value of the signal produced by circuit 25 reaches, or falls below, the target differential value, comparator 26 generates the tension control timing signal, and this signal is applied to produce operation of the drive mechanism and/or to supply a signal to electromagnetic generator 8, 9 to produce a force which cancels the strain value;

in the third procedure, if the output of strain measuring circuit 18 indicates a further change in the strength of specimen 1, caused by creep or the like, the second procedure is carried out again. If the output signal from strain measuring circuit 18 does not represent a further change in the strength of specimen 1, a measurement cycle is initiated by activating sinusoidal wave generator 23.

This application relates to subject matter disclosed in Japanese Application number 2-291052, filed on Oct. 29, 1990, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A tension type dynamic viscoelasticity measuring apparatus for measuring viscoelasticity of a specimen which has two opposed ends, said apparatus comprising:

a specimen holder for securely holding one end of the specimen;

a specimen chuck for securely holding the other end of the specimen;

a detection rod having two opposed ends, one of which ends is connected to said specimen chuck;

a strain detector operatively associated with said detection rod for detecting changes in position of said detection rod and producing an output signal representing the position of said detection rod relative to a reference position;

an electromagnetic force generator connected at one end of said detection rod to transmit a force to the specimen via said detection rod and said specimen chuck in response to a force signal;

a drive mechanism connected for moving said electromagnetic force generator in response to a movement signal;

electrical means for generating a force signal and for applying the force signal to said electromagnetic force generator;

movement control means for producing a movement signal and applying the movement signal to said drive mechanism for controlling the amount of movement of said drive mechanism;

signal differentiation means connected for receiving said output signal from said strain detector and producing a differential signal having a value corresponding to the time differential of said output signal from said strain detector;

a target differential value setter for providing a signal having a value corresponding to a selected value of the differential signal; and a comparator connected to receive the differential signal and the signal provided by said target differential value setter when the effective tension in the specimen continues to change for the duration of a relaxation phenomenon that has occurred as a result of the drive mechanism being moved or the electromagnetic force of the electromagnetic force generator being changed in order to control the tension at the specimen to maintain that tension substantially at a control target value;

whereby when the value of the differential signal from said strain differentiation circuit falls below the selected value, said comparator outputs a tension control timing signal indicating that the relaxation phenomenon has ceased.

2. Apparatus as defined in claim 1 wherein said electrical means comprise:

a dc generator for generating a tension force signal for causing said electromagnetic force generator to impose a tension in the specimen; and a sinusoidal wave generator for generating a sinusoidal wave force signal for causing said electromagnetic force generator to produce a sinusoidal force component.

* * * * *